US005429818A

United States Patent [19]

Inzana

[11] Patent Number: 5,429,818

[45] Date of Patent: Jul. 4, 1995

[54] **NON-CAPSULATED MUTANTS OF *ACTINOBACILLUS PLEUROPNEUMONIAE* USEFUL AS VACCINES**

[75] Inventor: Thomas J. Inzana, Blacksburg, Va.

[73] Assignee: The Center for Innovative Technology, Herndon, Va.

[21] Appl. No.: 83,311

[22] Filed: Jun. 24, 1993

Related U.S. Application Data

[63] Continuation of Ser. No. 803,044, Dec. 6, 1991.

[51] Int. Cl.[6] ........................ A61K 39/102; C12N 1/36

[52] U.S. Cl. .................................. 424/256.1; 424/825; 435/245; 435/243

[58] Field of Search ...................... 424/92, 256.1, 825; 435/245, 243

[56] References Cited

U.S. PATENT DOCUMENTS 5,149,529 9/1992 Ho .................................. 424/196.11

OTHER PUBLICATIONS

Murchison et al., Infect Immun., 34:1044–1055 (1981) Mutagenesis with EMS.

Izana et al., Infection and Immunity, 55:1573–1579 (1987) *H. pleuropneumoniae.*

Inzana et al., Infection and Immunity, 55:1580–1587 (1987) *H. pleuropneumoniae.*

Inzana et al., Infect. Immun., 56:1880–1889 (1988) *A. pleuropneumoniae.*

Inzana et al., J. Clin. Micr., 28:312–318 (1990) *A. pleuropneumoniae.*

Inmana et al., J. Clin, Micr., 28:1356–1361 (1990) (ELISA).

Inzana et al., Micro. Path., 10:281–296 (1991) *A. pleuropneumoniae.*

Rosendal et al., Am. J. Vet. Res., 51:711–717 (1990) Capsule–Deficient Mutant of serotype 1 *A. pleuropneumoniae.*

Devenish et al., Infect. Immun., 58:3829–3832 (1990).

Inzana, 11th Cong. Proc. Int. Pig Vet. Soc., Switzerland, Jul. 1–5, 1990.

Ma, J. et al. (1989) Abstr. Annu. Meeting Am. Soc. Microbiol. B180, p. 60.

*Primary Examiner*—Christine M. Nucker
*Assistant Examiner*—Julie Krsek-Staples
*Attorney, Agent, or Firm*—Whitham, Curtis, Whitham & McGinn

[57] ABSTRACT

Noncapsulated mutants of normally encapsulated bacteria in which the capsule is required for virulence are useful as vaccines for disease states caused by the normally encapsulated bacteria. In particular, a non-capsulated mutant of *Actinobacillus* (*Haemophilus*) *pleuropneumoniae* is useful in protecting against swine pleuropneumonia.

12 Claims, No Drawings

NON-CAPSULATED MUTANTS OF *ACTINOBACILLUS PLEUROPNEUMONIAE* USEFUL AS VACCINES

This is a Continuation of application Ser. No. 07/803,044 filed Dec. 6, 1991.

BACKGROUND OF THE INVENTION

1. Field of the Invention

The present invention is generally related to the use of non-capsulated mutants of normally encapsulated bacteria as a vaccine. In a particular application, the invention provides a low cost vaccine for pleuropneumonia and other diseases caused by encapsulated bacteria that produce exotoxins.

2. Description of the Prior Art

Vaccines are preparations used to prevent specific diseases in animals by inducing immunity. This is accomplished by exposing a patient to an antigen for a particular disease which, in turn, causes the immune system of the patient to produce large quantities of antibody. The presence of the antibody in the patient's blood protects the patient from a later attack by the disease causing agent. Vaccines may either be composed of subunits of the agent, or the live or killed agent itself. For example, poliomyelitis is typically controlled by either administering a live, attenuated oral poliovirus vaccine, which is common practice for treating children, or by administering a killed or inactivated poliovirus vaccine, which is the usual practice for treating adults since they generally have a higher risk of contracting polio from the live vaccine. If a live vaccine is to be used, its virulence must be attenuated in some way; otherwise, the vaccine will cause the disease it is intended to protect against.

A number of diseases are caused by encapsulated bacteria wherein the capsule, which is the gum-like layer of polysaccharide or polypeptide exterior to the cell wall of these bacteria, is required for pathogenesis. For example, pleuropneumonia, a serious respiratory disease affecting swine worldwide, is caused by *Actinobacillus pleuropneumoniae,* and it is has been determined that the serotype-specific antigen is the polysaccharide capsule (see, Inzana et al., *Infection and Immunity,* 55:1580–1587 (1987), which is herein incorporated by reference). In addition, in pneumonia of cattle caused by *Pasteurella haemolytica,* and respiratory disease of humans caused by encapsulated *Pseudomonas aeruginosa,* the polysaccharide capsules are also important in the virulence of these bacteria.

SUMMARY OF THE INVENTION

It is therefore an object of the invention to provide vaccines and methods of preparing vaccines which utilize non-capsulated mutants of normally encapsulated, toxigenic bacteria (bacteria that also produce protein exotoxins), wherein the capsule of such bacteria is required for virulence (e.g., swine pleuropneumonia, bovine pneumonia, and some respiratory disease of humans (cystic fibrosis)).

Swine pleuropneumonia due to *Actinobacillus pleuropneumoniae* is a highly contagious disease with major economic impact. *Actinobacillus pleuropneumoniae* virulence factors include capsular polysaccharide, endotoxin, and protein exotoxins. Commercial vaccines which consist of killed bacteria have been found to be inadequate for protection against pleuropneumonia. In addition, antibody to capsule has been found inadequate for complete protection, but the capsule is required for virulence. Non-capsulated mutants of several *Actinobacillus pleuropneumoniae* serotypes have been prepared by ethylmethanesulfonate mutagenesis. A deposit of stable non-capsulated mutants of *Actinobacillus pleuropneumoniae* serotype 5 has been made at the American Type Culture Collection (ATCC) under Accession No. 55454. These mutants are phenotypically identical to the parent strains, except for the complete lack of capsule production. Pigs immunized with the mutants have been shown to be protected against a later challenge with virulent *Actinobacillus pleuropneumoniae.* The protective effect has been observed with different serotypes of *Actinobacillus pleuropneumoniae.* In edition, the technique for producing the vaccines should be useful in protecting against other disease states, such as bovine pneumonia and human diseases caused by normally encapsulated, toxigenic bacteria.

DETAILED DESCRIPTION OF THE PREFERRED EMBODIMENTS OF THE INVENTION

Noncapsulated mutants of *A. pleuropneumoniae* can be prepared by in vitro passage or by chemical mutagenesis. The stable non-capsulated mutants of *A. pleuropneumoniae* are available from the ATCC under Accession No. 55454. In in vitro passage, several generation of the bacteria are streaked onto growth media and the resulting colonies are observed. Later generations of the bacteria are sometimes known to lose the polysaccharide capsule and colonies of these non-capsulated mutants can be identified by visual inspection of the colonies on the plate. In vitro passage can be used to obtain non-capsulated mutants of *A. pleuropneumoniae* serotype 5, strain K17, which is commercially available as the encapsulated parent bacterium from the American Type Culture Collection (ATCC). However, in vitro passage may usually cause a point mutation (mutation of a single or a few bases) and, therefore, produce strains that are only capsule deficient. Such strains may revert to their fully encapsulated phenotype when exposed to their normal host. Therefore, it is preferred that the non-capsulated mutants be obtained by direct chemical mutagenesis with ethyl methanesulfonate (EMS). It was by way of EMS mutagenesis that non-capsulated mutants of *A. pleuropneumoniae* serotype 5, strain J45, a strain isolated from a pig which died of pleuropneumonia identified at the University of California (the strain being available from Dr. Inzana at Virginia Polytechnic Institute and State University and Dr. Fenwick of Kansas State University), and *A. pleuropneumoniae* serotype 1, strain 4074, a strain available as the encapsulated parent bacterium from the ATCC, were prepared for use as a vaccine. Such chemical mutagenesis results in a deletion of deoxyribonucleic acid (DNA) required for encapsulation, and, therefore, is a far more stable mutation than those made by in vitro passage.

Mutagenesis with EMS is performed in a manner similar to that described in Murchison et al., *Infect Immun.,* 34:1044–1055 (1981). Briefly, bacteria are grown in brain heart infusion broth supplemented with 5μg/ml nicotinamide adenine dinucleotide (BHI-N), at 35° C. with shaking, to mid-log phase ($10^9$ colony forming units (CFU)/ml, determined by viable plate count) as is described by Inzana et al. in *Infect. Immun.,* 55:1573–79 (1987). Then 0.015 ml of EMS/ml of culture is added and the bacteria are incubated for an additional 2.5 hours. The bacteria are then washed three times in 0.01 M phosphate buffered saline (PBS) at pH 7.4 and resuspended in 1 ml of BHI-N. Undiluted and diluted suspensions of the mutagenized bacteria are spread on BHI-N plates and incubated at 35° C. for 24 to 48 hours. Colonies are selected that are non-iridescent when examined obliquely with a tungsten lamp, and are confirmed to be *A. pleuropneumoniae* by hemolytic activity and failure to grow on blood agar.

Suitable non-capsular mutants are phenotypically identical to the parent bacteria, except that they lack the gummy polysaccharide capsule on their external surface. Colonies of non-capsulated mutants lack iridescence when examined under oblique light. Viewing the colonies on a transparent plate at an angle to the light gives a rainbow light effect for encapsulated *A. pleuropneumoniae,* but provides no such effect for non-capsulated *A. pleuropneumoniae.* Hence, non-capsulated mutants can easily be distinguished from colonies of encapsulated bacteria.

The total capsule content can be determined by inhibition radioimmunoassay (RIA) of mid-log phase bacterial cultures (including bacteria and medium) as described in Inzana et al., *J. Clin. Microbiol.,* 28:312–318 (1990). The growth rate for both the parent and the non-capsulated mutants is approximately 30 min per generation. Electrophoretic profiles of lipopolysaccharide (LPS) and membrane proteins have been evaluated by one dimensional and two dimensional sodium dodecyl sulfate-polyacrylamide gel electrophorese (SDS-PAGE), respectively, followed by silver staining for LPS or proteins. Proteins have been analyzed in two dimensional gels and LPSs were analyzed in a 15% separating gel containing 3 M urea. The electrophoretic profiles of LPS and proteins were qualitatively identical. Hemolytic activity was determined by quantitative hemolysis assay and shown to be identical between the parent and the mutant. Table 1 shows the RIA measured capsule content of some of the strains and serotypes of encapsulated *A. pleuropneumoniae* and non-capsulated *A. pleuropneumoniae* prepared according to the above method.

TABLE 1

| STRAIN | Capsule content/ml[a] |
|---|---|
| J45 serotype 5 | 130 μg |
| J45 - capsule | <4 ng[b] |
| 4045 serotype 1[c] | 77 μg |
| 4045 - capsule | <4 ng |
| 4074 serotype 1 | 165 μg |
| 4074 - capsule | <4 ng |

[a]The bacteria in culture medium was at a density of $10^9$ CFU/ml. Capsule content is the mean of 3 determinations.
[b]4 ng/ml is the limit of detection of the RIA.
[c]*A. pleuropneumoniae* serotype 1, strain 4045, is another strain isolated from a pig which died of pleuropneumonia identified at the University of California.

Table 1 shows that the "non-capsular" mutants used in making the vaccines of the present invention truly lack capsule and are not merely "capsule deficient". Capsule deficiency usually indicates that bacteria do not appear encapsulated when measured by some procedures; however, some capsule may still be present and can be measured by sensitive assays (e.g., RIA). Such strains can revert to the fully encapsulated type when exposed to the natural host.

Table 2 presents present in vivo clinical results for several cross-bred pigs obtained from a local herd that were free of antibodies to pleuropneumonia.

TABLE 2

| GROUP | PIG ID | IMMUNIZED | CHALLENGED | ELISA pre | TITERS post | CLINICAL RESULTS |
|---|---|---|---|---|---|---|
| I | 227 | none | J45 | 1:800 | 1:800 | Increased respiration & lethargic; fibrinous adhesions (60%) to rt. thoracic wall, rt. lung 95% consolidated, lt. lung unaffected Ap+ |
| I | 222 | none | 4074 | 1:800 | 1:800 | Died; both lungs consolidated with some necrosis. Ap+ |
| II | 223 | bacterin | J45 | 1:800 | 1:800 | Abnormal respiration, reluctant to stand; ulcerated & squamous at site of tracheal injection, rt. lung 75% consolidated, lt. lung 60% Ap+ |
| II | 238 | bacterin | 4074 | 1:800 | 1:1600 | Elevated respiration, lethargic; focal adhesion to thoracic watt of 20% of rt. lung, rt. lung 30% consolidated, lt. lung 20% Ap? ND |
| III | 225 | 4074-C | J45 | 1:1600 | 1:6400 | Normal behavior; lt. lung congested, rt. lung normal Ap? ND |
| III | 221 | 4074-C | J45 | 1:800 | 1:1600 | Slightly lethargic; cellulitis at tracheal injection site, both lungs congested Ap? yes |
| III | 226 | 4074-C | J45 | 1:800 | 1:1600 | Normal behavior; lt. lung 20% consolidated, rt. lung normal Ap? ND |
| IV | 219 | J45-C | J45 | 1:800 | ND | Normal behavior & |

TABLE 2-continued

| GROUP | PIG ID | IMMUNIZED | CHALLENGED | ELISA TITERS pre | ELISA TITERS post | CLINICAL RESULTS |
|---|---|---|---|---|---|---|
| | | | | | | normal lungs Ap− (rt. & lt.) |
| IV | 224 | J45-C | J45 | 1:400 | 1:3200 | Normal behavior; lt. lung slightly congested, rt. lung normal Ap− (rt. & lt.) |
| IV | 220 | J45-C | J45 | 1:800 | 1:3200 | Elevated respiration, slightly lethargic; nodular areas of consolidation in both lungs Ap+ |
| V | 232 | J45-C & 4074-C | J45 | 1:800 | 1:6400 | Normal behavior; lt. lung 40% consolidated, 20% of rt. lung composed of focal points of consolidation Ap+ |
| V | 234 | J45-C & 4074-C | J45 | 1:800 | 1:1600 | Slightly lethargic; fibrinous adhesions to rt. thoracic wall and diaphragm, lt. lung 50% consolidated in focal areas, rt. lung congested Ap? ND |
| V | 228 | J45-C & 4074-C | J45 | 1:800 | 1:3200 | Lethargic, increased respiratory effort, focal area of consolidation (5% of lt. lung), focal areas of consolidation (20% rt. lung) Ap+ |
| VI | 235 | J45-C & 4074-C | 4074 | 1:800 | 1:3200 | Normal behavior, lt. lung 10% consolidated, rt lung normal Ap+ (rt.), − (lt.) |
| VI | 233 | J45-C & 4074-C | 4074 | 1:800 | 1:3200 | Normal behavior; lungs normal Ap− |
| VI | 239 | J45-C & 4074-C | 4074 | 1:800 | 1:1600 | Normal behavior; rt. lung 10% consolidated, lt. lung normal Ap− |
| VII | 236 | J45-C | 4074 | 1:400 | 1:3200 | Normal behavior; adhesion to thoracic wall at right caudal lobe, rt. lung 30% consolidated, lt. lung normal Ap+ |
| VII | 237 | J45-C | 4074 | 1:400 | 1:1600 | Shallow & increased respiration, lethargic; rt. lung 5% consolidated, lt. lung 30% consolidated with 30% of caudal lobe adhered to thoracic wall Ap+ |
| VII | 230 | J45-C | 4074 | 1:1600 | 1:3200 | Normal behavior; lt. lung 25% consolidated, rt. lung 10% consolidated Ap? ND |
| VIII | 231 | 4074-C | 4074 | 1:800 | 1:1600 | Respiration shallow & slow, lethargic; left lung 60% consolidated, rt. lung normal Ap− |
| VIII | 240 | 4074-C | 4074 | 1:800 | 1:1600 | Normal behavior; both lungs normal Ap− |
| VIII | 229 | 4074-C | 4074 | 1:200 | 1:1600 | Normal behavior, very small adhesions to thoracic wall on both lungs, lt. lung 20% consolidated, rt. lung 5% consolidated Ap? ND |

Sera from sows and piglets used in the studies were assayed for antibodies to serotypes 1 and 5 capsules by RIA, and for antibodies to hemolysin by enzyme linked immunosorbent assay (ELISA). All pigs used in the studies had titers in the negative range for normal animals to these antigens. Pigs were fed conventional feed during the investigation. Immunization injections were made subcutaneously one week after the pigs were obtained, and a second injection was made two to three weeks later. The groups of pigs were immunized with either diluent only, bacterin, a serotype 1 mutant, a serotype 5 mutant, or both the serotype 1 and serotype 5 mutant together. The subcutaneous doses of the serotype 1 and serotype 5 non-capsulated mutants included approximately $2*10^9$ CFU of the non-capsulated mutant suspended in PBS. The pigs were later challenged with either the serotype 1 parent or serotype 5 parent (*A. pleuropneumoniae* serotype 5, strain J45, or *A. pleuropneumoniae* serotype 1, strain 4074). For all challenge experiments, the bacteria were grown in supplemented Columbia broth to mid-log phase, centrifuged once, and resuspended to $10^9$ colony forming units (CFU)/ml in PBS. Viable plate counts were made prior to challenge to confirm challenge dose. Pigs were challenged intratracheally with 5 ml of the bacterial suspension following mild sedation with Stresnil (available from Pittman-Moore of New Jersey), and had a challenge dose of approximately $5*10^7$ CFU. The intratracheal challenge took place two to four weeks after immunization. The challenge was severe since $5*10^7$ cells were given in 5 mls of PBS intratracheally (directly into the lung), and this was done to test the limits of the vaccine. This challenge is far more severe than that would occur under field conditions.

For comparison purposes, two pigs were immunized with "bacterin". A bacterin is a washed, killed suspension of bacteria mixed with a strong adjuvant, such as an oil based emulsion. The source of bacterin used was Beecham Laboratories, Bristol, Tenn., and is called Pneumosuis III. The limited protection provided by pleuropneumonia vaccines such as bacterin are serotype specific, therefore more than one serotype needs to be included. Since the bacteria are killed, there is no hemolysin present in the vaccine (because essentially all the hemolysin is exported from the cell). Therefore, pigs immunized with bacterin lack antibody to hemolysin, which was found to be required for maximum protection (see, Inzana et al., *Microbial Pathogenesis*, 10:281-296 (1991), which is herein incorporated by reference).

ELISA experiments were performed as described in Ma and Inzana, *J. Clin. Microbiol.*, 28:1356-1361 (1990), and that article is incorporated by reference. The ELISA results are based on a test comparing the pigs' serum prior to immunization and serum immediately prior to the bacterial challenge and provides a measure of hemolytic titers. Pigs were bled before the first injection and again just prior to challenge with the virulent encapsulated bacteria (two to four weeks after the second injection). The ELISA assay measures antibody to hemolysin, which is the primary virulence factor of these bacteria. It was determined that pigs having substantial antibody titers to hemolysin were generally better protected against disease.

The clinical results include subjective observations of the pigs' behavior on the morning following challenge. The necropsy results and *A. pleuropneumoniae* recovery from cultures reported in the right most column of Table 2 are from lung taken from the respective pigs. If a culture was not taken from the animal, a "ND" appears in this right most column to indicate "not determined". For several of the animals, a culture was taken from each lung because one lung appeared very different from the other lung in terms of degree of consolidation and congestion. In these cases, *A. pleuropneumoniae* recovery is indicated in each respective lung (i.e., "lt" indicates left lung and "rt" indicates right lung). Except for the surviving negative control, the two pigs in Group II which received the commercial "bacterin" immunization, and pigs #221 of Group III and #231 of Group VIII, the pigs vaccinated with attenuated *A. pleuropneumoniae* were clinically normal. The condition of the sick pigs immunized with the live vaccine following the challenge improved to normal (clinically) within two days following administration; control and bacterin immunized pigs did not. For this reason, the control and bacterin immunized pigs were euthanized and necropsied first at four days following the challenge. The remainder of the pigs were euthanized and necropsied in random order over the following two days.

With particular reference to Table 2, it can be seen that pigs which were not immunized (e.g., those in Group I) suffered the effects of pleuropneumonia when challenged with either *A. pleuropneumoniae* serotype 5, strain J45, or *A. pleuropneumoniae* serotype 1, strain 4074. Specifically, pig #222 died with both lungs consolidated and pig #227 suffered increased respiration and lethargy. It was later determined that the right lung of pig #227 was 95% consolidated and had fibrinous adhesions to the right thoracic wall. *A. pleuropneumoniae* was recovered in both pig #227 and pig #222. Pigs in Group II which were immunized with the commercial "bacterin", containing killed bacteria of both serotypes 1 and 5, were not protected from either *A. pleuropneumoniae* serotype 5, strain J45, or *A. pleuropneumoniae* serotype 1, strain 4074 challenge. Both pigs suffered from abnormal or elevated respiration and lung consolidation.

In sharp contrast, Table 2 further shows that the Group IV pigs (#219, #224, #220), which were immunized with non-capsulated mutants of *A. pleuropneumoniae* serotype 5, strain J45 (e.g., "J45-C"), and the Group VIII pigs (#240, #229), which were immunized with non-capsulated mutants of *A. pleuropneumoniae* serotype 1, strain 4074 (e.g., "4074-C"), were generally protected when challenged later with the encapsulated J45 and 4074 strains of the bacteria. Pig #231 of Group VIII was unique because it gained only six pounds during the study and was, therefore, not as inherently healthy with respect to other pigs which were examined. Hence, this factor may explain the degree of sickness expressed in this animal following challenge. Likewise, Table 2 shows that the Group V pigs (#232, #234, #228) and the Group VI pigs (#235, #233, #239), which were each immunized with a combination of non-capsulated mutants for both *A. pleuropneumoniae* serotype 5, strain J45, and the *A. pleuropneumoniae* serotype 1, strain 4074 (e.g., both J45-C and 4074-C), were generally protected when later challenged by either of the encapsulated bacteria (e.g., J45 or 4074). The increased respiratory effort, lethargy and lung consolidation observed is probably the result of the very severe test conditions used (e.g., intratracheal challenge with a large number of bacteria) which were chosen to discern the limits of the vaccine. Hence, the less severe challenges which will be encountered in the field will be expected to have minimal effect on an animal immunized with this vaccine.

Vaccines with more than one serotype of non-capsulated mutants may prove advantageous; however, the data presented shows that vaccines with only one serotype of non-capsulated mutant may be suitable. Table 2 shows that immunization with non-capsulated mutants of one serotype of *A. pleuropneumoniae* can have beneficial effects when challenged with encapsulated bacteria of *A. pleuropneumoniae* of another serotype. In particular, Table 2 shows that Group III pigs immunized with non-capsulated mutants of serotype 1 4074-C were generally protected when later challenged with serotype 5 J45 *A. pleuropneumoniae.*

Several variables were examined to determine the optimum dose, route, and method of immunization of the non-capsulated mutants. In particular, non-capsulated mutants of *A. pleuropneumoniae,* serotype 5, strain J45, were administered in various doses either subcutaneously, intradermally, or intranasally for one or several immunizations. The non-capsulated mutants were suspended in 7% mucin, microargarose beads, Freund's Incomplete Adjuvant, or PBS for subcutaneous and intradermal immunizations, and PBS only for intranasal immunizations. The time the non-capsulated mutants could survive following immunization in each site and in each medium was determined, as well as the immune response. In addition, some pigs were immunized subcutaneously with mutants in capsule implants. As above, the pigs were challenged two to four weeks after the final immunization. Serum for antibody titers to non-capsulated whole cells were obtained prior to immunization and again at the time of challenge. Antibody titers were determined for non-capsulated whole cells by ELISA, for hemolysin by indirect ELISA, and for capsule by ELISA or RIA.

Table 3 shows the virulence of non-capsulated *A. pleuropneumoniae,* serotype 5, strain J45, for pigs by intranasal and intratracheal challenge.

TABLE 3

| Challenge Route | Postchallenge Time[a] | Mortality | Lesions | Recovery of AP[b] |
|---|---|---|---|---|
| Intra-tracheal[c] | 5 days | 0/3 | 0/3 | 0/3 |
| Intranasal[e] | 3 days | 0/2 | 0/2 | 0/2[d] |
| Intranasal[e] | 7 days | 0/2 | 1/2[f] | 1/2[g] |
| Intranasal[h] | 1 day | 0/3 | 0 /3 | 0/3 |

[a]Postchallenge time was the number of days from challenge to necropsy.
[b]AP stands for *A. pleuropneumoniae.*
[c]Pigs were challenged intratracheally with 5*10[7] CFU in 10 ml PBS (this is 75–100% of lethal dose for parent).
[d]Nasal swabs, tonsils, trachea, and lung samples were obtained from all pigs challenged intranasally.
[e]Pigs were challenged with 2.5 ml/nostril containing a total of 10[8] CFU in PBS.
[f]One pig had slight pneumonia and pleuritis.
[g]AP was recovered only from one lung of the pig with slight pneumonia and was still noncapsulated.
[h]Pigs were challenged with 0.5 ml/nostril containing a total of 10[8] CFU in PBS.

Table 3 shows that the non-capsulated mutants are well tolerated at high concentrations regardless of the manner by which they are delivered.

Table 4 shows the survival, immunogenicity, and protective efficacy of non-capsulated *A. pleuropneumeniae,* serotype 5, strain J45, in various suspending media.

TABLE 4

| MEDIUM[a] | INCUBATION CONDITIONS/SITE[b] | SURVIVAL TIME[c] | HEMOLYSIN TITER[d] pre | post | MORTALITY | LESIONS[e] |
|---|---|---|---|---|---|---|
| PBS | In vitro | >4 days | 80–160 | >1280 | 0/3 | none (2) |
| | Subcutaneous | >7 days | | | | pneumonia (1) |
| | Intradermal[f] | >7 days | | | | |
| | Intranasal | <1 day[g] | | | | |
| FIA | In vitro | >4 days | 80–160 | >1280 | 0/3 | none (1) |
| | Subcutaneous | >7 days | | | | pneumonia (2) |
| | Intradermal | >7 days | | | | |
| 7% Mucin | In vitro | >4 days | 80–160 | >1280 | 0/9 | pneumonia (5) |
| | Subcutaneous | >7 days | | | | |
| | Intradermal | >7 days | | | | |
| Microager-ose beads | In vitro | >4 days | 160 | 320 | 3/3 | pneumonia (3) |
| Capsule implants | Subcutaneous | >6 weeks | 160 | 320–640 | 0/2 | pneumonia (2) |

[a]PBS - phosphate buffered saline; FIA - Freund's Incomplete Adjuvant.
[b]The subcutaneous and intradermal immunization dose was 2 × 10[9] CFU, and the intranasal immunization dose was 10[8] CFU of J45-C. The challenge dose was 5 × 10[7] CFU of J45 (75–100% lethal dose).
[c]Some pigs were necropsied 1, 3 and 7 days after immunization, and the immunization site cultured for surviving bacteria. Other pigs were challenged 2 weeks after a second immunization.
[d]Immune response to whole cells was similar or greater than the response to hemolysin. Neutralizing hemolysin titers paralleled ELISA titers. Pigs with less than a six fold increase in ELISA titer did not have significant neutralizing titers, whereas pigs with titers >1280 did have neutralizing titers.
[e]Number in parenthesis indicates the number of pigs with slight to severe pneumonia. Bacteria were recovered from all pneumonic lungs. Pigs with slight pneumonia were clinically normal. Pigs with moderate to severe pneumonia demonstrated some clinical illness.
[f]Intradermal immunizations resulted in more severe inflammation and necrosis at the injection site than subcutaneous immunizations.
[g]Of 7 pigs immunized intranasally, bacteria were recovered from the lungs of 1 pig, 7 days after immunization, but not from lungs or trachea of any pigs, 1 or 3 days after immunization.-.

From Table 4 it can be seen that viable, non-capsulated mutants can be recovered from PBS or various adjuvants after more than four days incubation in vitro or more than one week after subcutaneous or intradermal immunization. The non-capsulated mutants survived in vivo for at least six weeks in capsular implants and remained non-capsular. However, they could not be recovered from the respiratory tract one day after intranasal immunization.

Table 5 is a table showing the protective efficacy of non-capsulated *A. pleuropneumoniae* serotype 5, strain J45, in PBS in relation to the dose and number of subcutaneous immunizations.

TABLE 5

| DOSE | NUMBER OF IMMUNIZATIONS[a] | MORTALITY | IMMUNIZATION SITE[b] | LUNG LESIONS[c] | RISE IN TITER HEMOLYSIN | CELLS |
|---|---|---|---|---|---|---|
| 8 × 10[7] CFU[d] | 1 | 1/1 | normal | >60% | none | 8 fold |
| 4 × 10[8] CFU[d] | 1 | 1/1 | normal | >50% | 2 fold | 4 fold |

TABLE 5-continued

| DOSE | NUMBER OF IMMUNIZATIONS[a] | MORTALITY | IMMUNIZATION SITE[b] | LUNG LESIONS[c] | RISE IN TITER HEMOLYSIN | RISE IN TITER CELLS |
|---|---|---|---|---|---|---|
| $2 \times 10^9$ CFU[d] | 1 | 0/1 | Sl. abscess | 7% | 8 fold | >8 fold |
| $5 \times 10^8$ CFU[e] | 1 | 3/3 | ND | ≧50% | none - 2 fold | 4-8 fold |
| $5 \times 10^8$ CFU[e] | 2 | 3/3 | ND | ≧50% | none - 4 fold | 4-8 fold |
| $1 \times 10^9$ CFU[e] | 1 | 3/3 | ND | 20-65% | none | 2 fold |
| $1 \times 10^9$ CFU[e] | 2 | 3/3 | ND | 20-80% | 2-4 fold | 8-32 fold |
| $2 \times 10^9$ CFU[e] | 3 | 0/3 | Sl. abscess | 0-50%[f] | >16 fold | ≧16 fold |

[a]Pigs given 1 immunization were challenged 4 weeks later. Pigs given 2 or 3 immunizations were challenged 2 weeks after the last immunization.
[b]The immunization site was examined at necropsy and evaluated for the extent of abscess formation.
[c]Described as the percent of lung area with pneumonic lesions.
[d]The bacteria were divided and administer in 2 sites.
[e]The bacteria were all administered in 1 site.
[f]Two pigs had normal lungs and 1 pig had pneumonia with about 50% involvement.
Sl - Slight.
ND - not determined.--.

The strongest immune response and protection occurred when the bacteria were suspended in Freund's Incomplete Adjuvant or PBS. The best protection with minimal tissue damage was obtained following two or more subcutaneous immunizations with $2*10^9$ CFU/ml of mutant in PBS. Protection correlated well with an eight fold increase or greater in the ELISA hemolysin titer.

As can be seen from Table 2, non-capsulated mutants of the toxigenic, normally encapsulated *A. pleuropneumoniae* bacteria provide effective protection against pleuropneumonia. In these bacteria, the capsule is required for virulence. However, it is the exotoxins produced by the bacteria that cause the lesions and symptoms of disease. Therefore, it is postulated that immunization with non-capsulated mutants causes the swine to produce antibodies of the exotoxins in the non-capsulated mutants without the virulence encountered when the capsule is present. The antibodies thus produced then protect the swine when encapsulated *A. pleuropneumoniae* are encountered. As shown in Table 2, the protective abilities of the vaccine were noted for two different strains, each for different serotypes, of bacteria. Other diseases caused by toxigenic, normally encapsulated bacteria where the capsule is required for virulence (e.g., pneumonia in cattle, cystic fibrosis in humans) would be treatable by similar vaccines wherein non-capsulated mutants are prepared by chemical mutagenesis or in vitro passage of the parents since the mode of operation in those diseases is related to the exotoxins produced by the bacteria and the capsule is required for virulence. As shown in Table 3 above, high doses of the non-capsulated mutants are well tolerated. As shown in Table 3 and Table 4, the non-capsulated mutants can survive for extended periods of time subcutaneously in vivo and in vitro, and the vaccine is safe because the mutants are stable and cannot be recovered from the respiratory tract.

In *A. pleuropneumoniae* and other bacteria that produce capsules and also exotoxins, the capsule protects the organism from host defenses (e.g., antibody and complement-mediated killing, and phagocytosis and phagocytic cells). The capsule itself does not contribute to the disease; rather, it only protects the organism from host defenses. Therefore, without the capsule the bacterium is not virulent (it cannot cause disease). However, in bacteria that also produce exotoxins, the toxins are responsible for the lesions and the pathology of the disease. Therefore, antibodies to the hemolysin are needed to neutralize the activity of the toxins. Antibody to capsule alone may actually cause more harm than good because the bacteria may be concentrated in phagocytic cells by antibodies to capsule, but without antibodies to toxin, the toxin may kill the phagocytic cells and cause more severe damage due to release of inflammatory mediators from the host cells.

The vaccines described herein are ideal because: (1) antibodies to the capsule are not made; therefore, immunized animals can be differentiated from infected animals by serologic tests; (2) the bacteria are avirulent and cannot survive in the respiratory tract, and the mutation is stable, therefore, they are safe; (3) high titers of antibody to hemolysins and other somatic antigens (e.g., LPS or endotoxin) are made (these antibodies neutralize the effects of toxin to protect the animal); and (4) the mutant bacteria can survive for long periods subcutaneously, thereby enabling a good immune response to be made. The protection afforded by this vaccine may also provide some cross-reactive protection against other bacteria that produce related exotoxins. For example, *Actinobacillus suis* is known to produce a toxin that is very similar and cross-reacts with hemolysin of *A. pleuropneumoniae*. Therefore, immunization with this mutant may provide protection against disease caused by *A. suis*. In addition, protection of other animals and humans against other encapsulated, toxigenic bacteria would apply (e.g., Pasteurella pneumonia in cattle and *Pseudomonas aeruginosa* infections of humans and animals).

The vaccine would be provided in a form similar to other vaccines well known in the art. It is preferable that the vaccine would be bottled as a lyophilized mixture of one or more serotypes of mutant strains. To preserve viability, a protein, glycerol, or some other agent would be included. These experiments showed Columbia broth was acceptable, but it is expected that other mediums with high protein content such as albumin would also be acceptable. The contents of the vial would only need to be rehydrated with sterile water or saline and injected.

While the invention has been described in terms of its preferred embodiments, those skilled in the art will recognize that the invention can be practiced within the spirit and scope of the appended claims.

Having thus described my invention, what I claim as new and desire to secure by Letters Patent is as follows:

1. A subcutaneous or intradermal vaccine, comprising a noncapsulated mutant of *Actinobacillus pleuropneumonia* having ATCC Accession Number 55454, in an adjuvanted or buffered medium, in an amount which induces safe and protective immunity in swine against disease caused by normally encapsulated *Actinobacillus pleuropneumoniae* bacteria.

2. The vaccine of claim 1, wherein said adjuvanted medium includes Freund's incomplete adjuvant.

3. The vaccine of claim 1 wherein said buffered medium includes phosphate buffered saline.

4. The vaccine of claim 1 wherein said noncapsulated mutant is at a concentration of $2\times10^9$ CFU/ml.

5. The vaccine of claim 2 wherein said noncapsulated mutant is at a concentration of $2\times10^9$ CFU/ml.

6. The vaccine of claim 3 wherein said noncapsulated mutant is at a concentration of $2\times10^9$ CFU/ml.

7. A method of inducing protective immunity in swine against disease caused by *Actinobacillus pleuropneumoniae* comprising the step of subcutaneously or intradermally administering a stable non-capsulated mutant of *Actinobacillus pleuropneumoniae* having ATCC Accession Number 55454 in an adjuvanted or buffered medium to swine in an amount so that said non-capsulated mutant induces safe and protective immunity in said swine against the disease.

8. The method of claim 7, wherein said administering comprises two or more subcutaneous administrations of said noncapsulated mutant at a concentration of $2\times10^9$ CFU/ml.

9. The method of claim 7 wherein said adjuvanted medium includes Freund's incomplete adjuvant.

10. The method of claim 7 wherein said buffered medium includes phosphate buffered saline.

11. The method of claim 8 wherein said adjuvanted medium includes Freund's incomplete adjuvant.

12. The method of claim 8 wherein said buffered medium includes phosphate buffered saline.

* * * * *